(12) United States Patent
Du et al.

(10) Patent No.: US 9,726,651 B2
(45) Date of Patent: Aug. 8, 2017

(54) DOUBLE-SIDED DIAPHRAGM MICRO GAS-PRECONCENTRATOR WITH A BACK-ON-FACE CONFIGURATION

(71) Applicant: University of Electronic Science and Technology of China, Chengdu, Sichuan (CN)

(72) Inventors: Xiaosong Du, Sichuan (CN); Luhua Cheng, Sichuan (CN); Penglin Wu, Sichuan (CN); Huan Yuan, Sichuan (CN); Yadong Jiang, Sichuan (CN); Ze Wu, Sichuan (CN); Yi Li, Sichuan (CN); Dong Qiu, Sichuan (CN)

(73) Assignee: University of Electronic Science and Technology of China, Chengdu, Sichuan (CN)

( * ) Notice: Subject to any disclaimer, the term of this patent is extended or adjusted under 35 U.S.C. 154(b) by 391 days.

(21) Appl. No.: 14/593,304

(22) Filed: Jan. 9, 2015

(65) Prior Publication Data
US 2015/0160172 A1 Jun. 11, 2015

Related U.S. Application Data

(62) Division of application No. 13/570,249, filed on Aug. 9, 2012, now Pat. No. 8,969,976.

(30) Foreign Application Priority Data

Mar. 23, 2012 (CN) .......................... 2012 1 0078853

(51) Int. Cl.
*G01N 30/08* (2006.01)
*H01L 27/02* (2006.01)
(Continued)

(52) U.S. Cl.
CPC ............ *G01N 30/93* (2013.01); *B01L 3/5027* (2013.01); *G01N 1/405* (2013.01); *G01N 1/4005* (2013.01);
(Continued)

(58) Field of Classification Search
CPC ...... G01N 30/93; G01N 1/4005; G01N 1/405; G01N 30/08; G01N 2030/085;
(Continued)

(56) References Cited

U.S. PATENT DOCUMENTS

2003/0231967 A1* 12/2003 Najafi ................... F04B 45/047
                                                                 417/322

* cited by examiner

*Primary Examiner* — Selim Ahmed

(57) ABSTRACT

A double-sided diaphragm micro gas-preconcentrator has a micro-gas chamber which is formed by stacking an upper silicon substrate with a lower silicon substrate with a back-on-face configuration. One or more suspended membranes are provided on every silicon substrate. The silicon where the suspended membrane is provided is completely removed for forming a cavity. A thin-film heater is deposited on every suspended membrane. A sorptive film is coated on an inner wall of every suspended membrane. Thus, the upper and lower sides of the preconcentrator in the present invention are suspended membranes, which improve the area of the sorptive film on the diaphragm. As a result, the preconcentrating factor is improved while keeping the small heat capacity, fast heating rate, and low power consumption features of the planar diaphragm preconcentrator.

8 Claims, 7 Drawing Sheets

(51) Int. Cl.
*G01N 30/93* (2006.01)
*B01L 3/00* (2006.01)
*G01N 1/40* (2006.01)

(52) U.S. Cl.
CPC ........ *G01N 30/08* (2013.01); *B01L 3/502707* (2013.01); *B01L 2300/069* (2013.01); *B01L 2300/0816* (2013.01); *B01L 2300/0864* (2013.01); *B01L 2300/0883* (2013.01); *G01N 2030/085* (2013.01)

(58) Field of Classification Search
CPC ............. B01L 3/5027; B01L 2300/069; B01L 2300/0816; B01L 2300/0864; B01L 2300/0883; B01L 3/502707
USPC .......................................... 257/414, E27.009
See application file for complete search history.

DOUBLE-SIDED DIAPHRAGM MICRO GAS-PRECONCENTRATOR WITH A BACK-ON-FACE CONFIGURATION

CROSS-REFERENCE TO RELATED APPLICATION

This is a divisional application of U.S. patent application Ser. No. 13/570,249, filed Aug. 9, 2012.

BACKGROUND OF THE PRESENT INVENTION

Field of the Invention

The present invention relates to a gas preconcentrator, and more particularly to a micro gas preconcentrator manufactured by MEMS technology.

Description of Related Arts

It is needed for a gas sensor with high sensitivity, high selectivity, fast response, low power and portability to detect the trace level of industrial pollution, high explosives, drugs, and chemical and biological toxic agents for field analysis. However, it is difficult to meet the above mentioned requirements relying solely on the gas sensor itself. Therefore, it is compulsorily for a micro-preconcentrator to be introduced in the front end of the gas sensor for improving the sensitivity, a micro-chromatography to be incorporated for improving the selectivity. As a result, a plurality of components is combined into an integrated gas detector.

The preconcentrator has been widely used for many years in analytical chemistry. It collects and accumulates one or more chemical species of interest by passing the low concentration vapor stream through the sorptive material for a period of time. The sorptive layer is subsequently heated and the thermally released analyte provides narrow desorption peaks with relatively high concentration. The preconcentrator can improve not only the sensitivity of the detector for 1-3 orders of magnitude, but also the selectivity of the detector to the special target by the chemoselective sorptive film.

Besides the intrinsic characteristics of the sorptive film, the concentration factor of the preconcentrator is predominately determined by flow rate, heating rate and the area of the sorptive film. For a given amount of gas molecules collected on the sorptive film, the faster the heating rate, the higher the gas desorption peak intensity and the narrower the full width at half maximum (FWHM). To realize rapid heating, the preconcentrator with low heat capacity is preferred, and in principle fabricated by MEMS technology. The literature of "Trends in Analytical Chemistry, 2008, 27(4):327-343" systematically summarizes the research status of the MEMS gas preconcentrator in recent years.

In all micro-preconcentrators, the two-dimensional diaphragm preconcentrator disclosed by U.S. Pat. No. 6,171,378 (as shown in FIG. 1A) has the smallest heat capacity. For the SiN diaphragm with the thickness of 0.5 μm, it can be heated up to 200° C. under the power of 100 mW for 10 ms and the FWHM of the gas desorption peak is only 200 ms. However, the above mentioned planar preconcentrator has prominent drawbacks. Firstly, the sorptive film has small area. Secondly, the flow rate is too low while preconcentrating. As a result, the preconcentration factor of the 2D planar preconcentrator is far lower than that of the conventionally tubular preconcentrator (which can refer to FIG. 4b in the literature IEEE Sensor Journal, 2006, 6(3): 784-795).

U.S. Pat. Nos. 7,118,712 and 7,306,649 disclosed 3D preconcentrators. A plurality of perforations acting as gas flow channels are formed on a three-dimensional material with a substantial thickness, and the sorptive film is coated on the inner walls of the gas flow channels. Compared with the 2D diaphragm preconcentrator, the surface area of the sorptive film of the 3D preconcentrator can be increased by tens of times, and the gas flow rate thereof can also be enhanced greatly. The clamshell preconcentrator (as shown in FIG. 1B) is a typical representative of the 3D preconcentrators. It uses the fin-shaped parallel grooves as the sorption support structure for increasing the area of the sorptive film, resulting in equal preconcentration factor with respect to the tubular preconcentrator. The clamshell preconcentrator also has suspended membranes. The thin-film heater and the fin-shaped sorption support structure are respectively disposed on two sides of each membrane. In spite of the above mentioned heat insulation design, the heat capacity of the clamshell preconcentrator increases remarkably due to the fin-shaped bulk structure. Consequently, the FWHM of the gas desorption peak is extended to 2.3 s (which can refer to FIG. 4b of the literature IEEE Sensor Journal, 2006, 6(3): 784-795).

In an integrated gas detector, a micro-chromatography is needed to be incorporated at the downstream end of a micro-preconcentrator. In such a case, the preconcentrator must also act as an injector of a conventional chromatograph. The preconcentrator is required to desorb the accumulated chemical molecules as quickly as possible. Otherwise, the GC peaks will be broadened, thereby reducing the performance of the chromatography. Obviously, the 3D preconcentrators elevate their preconcentration factor at the expense of rapid heating capability, thus can not meet the demands of an integrated gas detector.

The diaphragm of the 2D preconcentrator tends to break during rapid heating since the inlet/outlet holes provided on the glass lid is too small. The perforated structure of the 3D preconcentrators greatly increases the sectional area of the flow channel, thereby improving the flow rate. However, in the various embodiments disclosed by U.S. Pat. No. 7,118,712 (as shown in FIG. 1B), the three-dimensional sorption support structures are suspended on a layer of thin diaphragm. Hence, the diaphragm is subject to a large static stress and at the risk of rupture.

SUMMARY OF THE PRESENT INVENTION

The present invention directly addresses the problems describe above, aiming at a higher preconcentration factor by enlarging the effective area of the sorptive film at the same device size, while keeping the low heat capacity, fast heating speed, and low power consumption features of the 2D diaphragm preconcentrator.

Accordingly, in order to accomplish the above object, the present invention provides a double-sided diaphragm micro gas-preconcentrator, comprising two silicon substrates, wherein at least one suspended membrane is disposed on each silicon substrate; a thin-film heater is prepared on every suspended membrane; at least one micro-gas chamber is formed by aligning and bonding the two silicon substrates; a sorptive film is coated on the innerside wall of every suspended membrane; and gas holes are provided at sidewalls of the micro-gas chamber for forming airflow channels among a plurality of micro-gas chambers, or an air inlet or air outlet of the whole preconcentrator.

The double-sided diaphragm micro gas-preconcentrator provided by the present invention is characterized in that the suspended membrane is a silicon nitride film or silicon oxynitride film or $SiO_2$ film or $SiN/SiO_2$ multilayer film with a thickness of 0.5-2 μm.

The double-sided diaphragm micro gas-preconcentrator provided by the present invention is characterized in that the thin-film heater is a serpentine metal thin film or a heavily doped polysilicon thin film, and the metal thin film is made of platinum or palladium or tungsten or molybdenum or tantalum.

The double-sided diaphragm micro gas-preconcentrator provided by the present invention is characterized in that the sorptive film is made of polymer or carbon black/polymer composite materials or sol-gel inorganic oxides.

The present invention is an improvement on the prior 2D membrane preconcentrator. In the present invention, the suspended membranes are respectively disposed on the upper and lower sides of the micro-gas chamber, whereon the sorptive film is coated, thus, the area of the sorptive film is doubled without changing the size of the preconcentrator, thereby obtaining a micro gas-preconcentrator with higher preconcentration factor.

These and other objectives, features, and advantages of the present invention will become apparent from the following detailed description, the accompanying drawings, and the appended claims.

wherein, 1: silicon base; 2: silicon cover; 3: suspended membrane; 4: thin-film heater; 5: sorptive film; 6: air inlet; 7: air outlet; 8: silicon substrate; 9: SiN film; 10: cavity; 11: adhesive layer; 12: micro-gas chamber; 13: airflow through-hole; 14: airflow distribution network.

DETAILED DESCRIPTION OF THE PREFERRED EMBODIMENT

The double-sided diaphragm micro gas-preconcentrator of the present invention has two types, namely, the preconcentrator and the preconcentrator array. The feature is that the suspended membranes prepared on two silicon substrates are aligned with each other and then bonded together for forming a micro-gas chamber, Hence, the upper and lower inner walls of the gas chamber are coated with the sorptive film. The present invention is further explained in detail with the accompanying drawings.

Embodiment 1

Figure 1A:
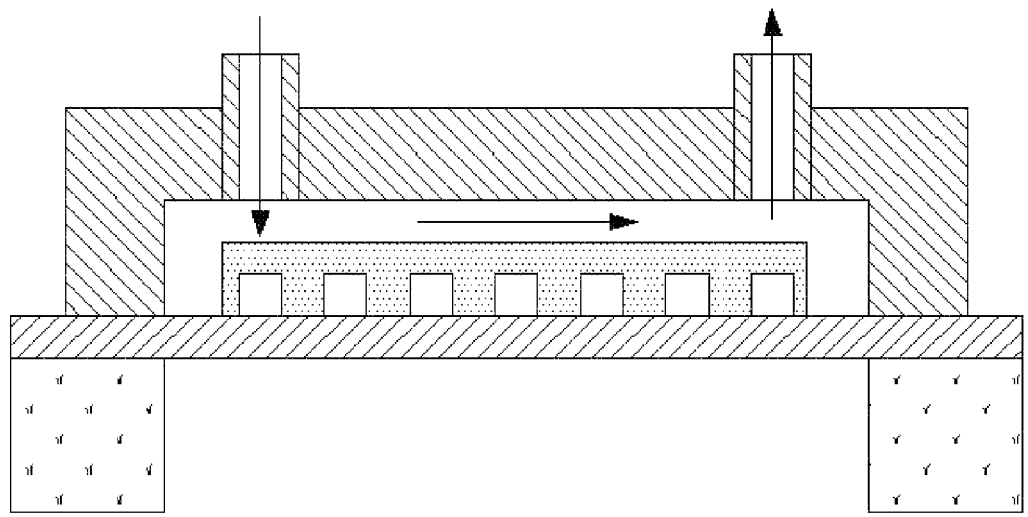
FIG. 1A is the 2D single diaphragm preconcentrator of prior art.
Figure 1B:
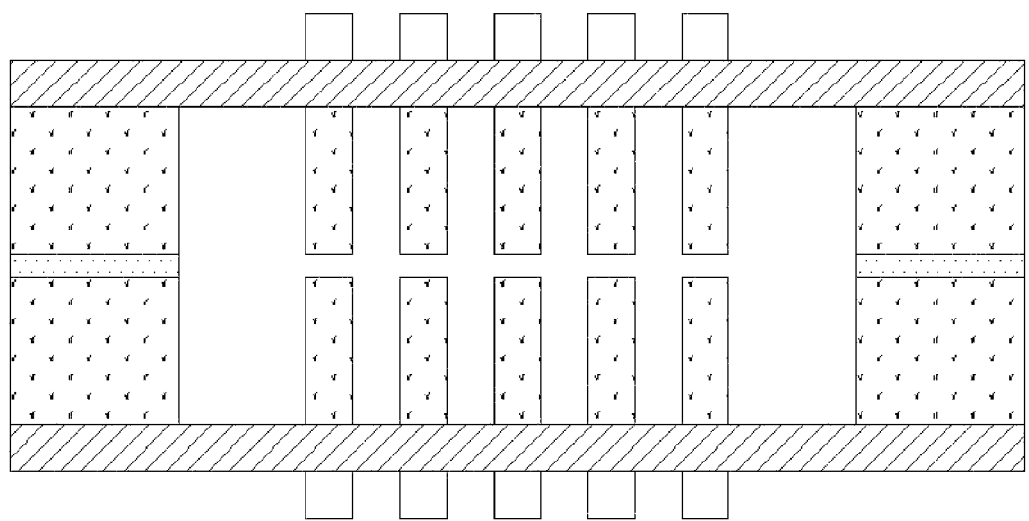
FIG. 1B is the 3D clamshell-shaped preconcentrator of prior art.
Figure 2A:
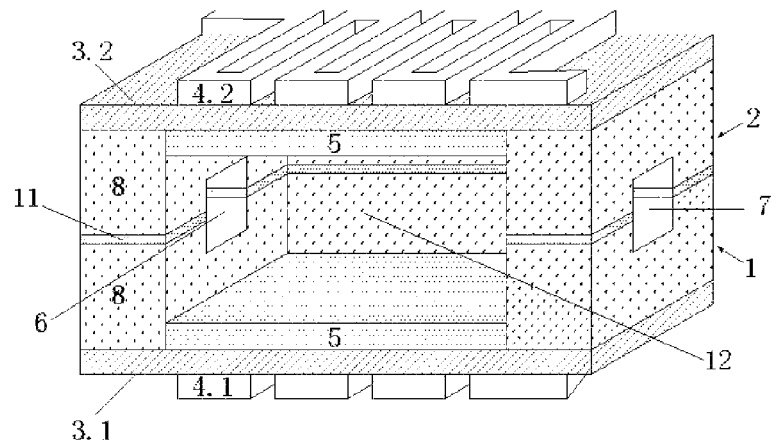
FIG. 2A shows a stereogram of a double-sided diaphragm micro gas-preconcentrator according to a first preferred embodiment of the present invention.
Figure 2B:
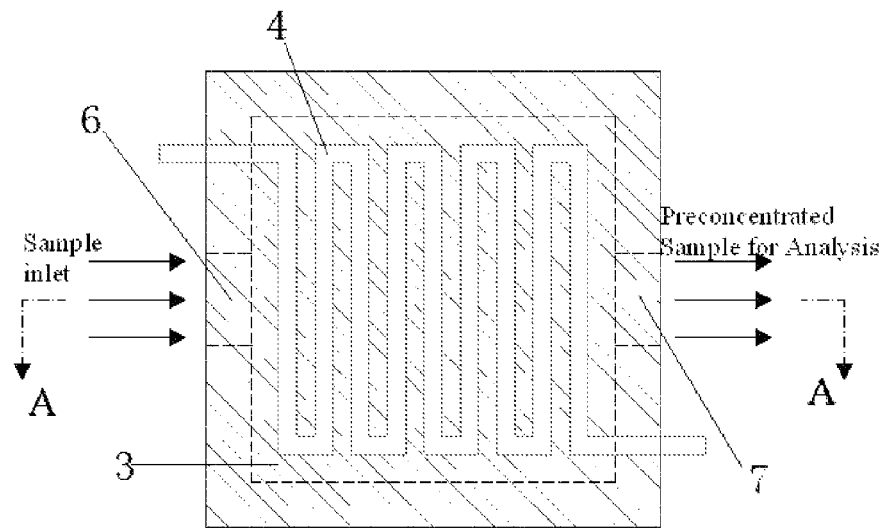
FIG. 2B is a top view of the double-sided diaphragm micro gas-preconcentrator according to the above first preferred embodiment of the present invention.
Figure 2C:
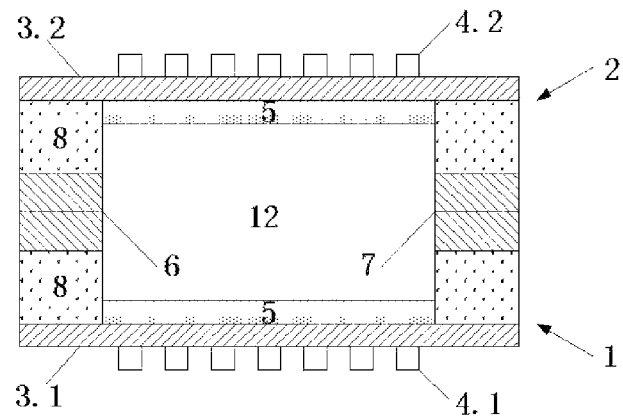
FIG. 2C is a sectional view along A-A direction of FIG. 2B.
Figure 3:
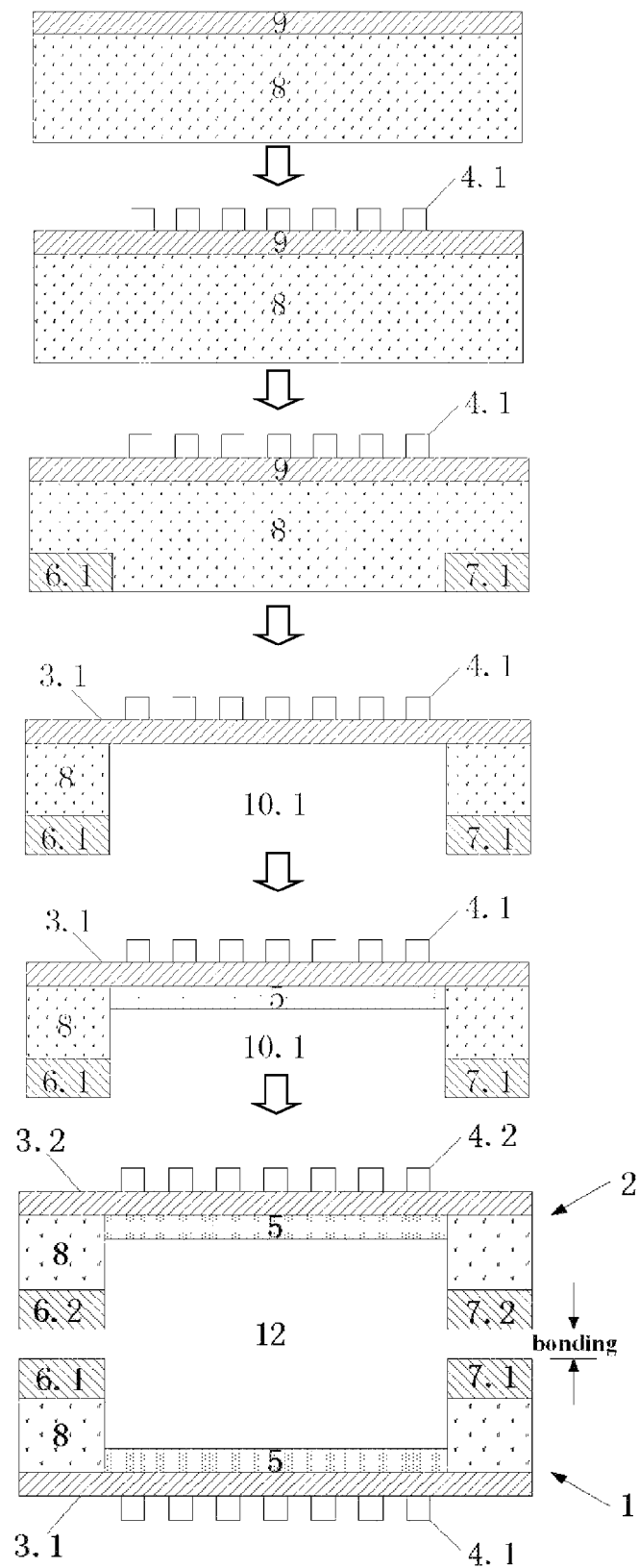
FIG. 3 is a flow chart of the MEMS preparation process of the double-sided diaphragm micro gas-preconcentrator according to the above first preferred embodiment of the present invention.

FIGS. 2A to 2C are schematic views of a double-sided diaphragm micro gas-preconcentrator according to the first preferred embodiment of the present invention. The double-sided diaphragm micro gas-preconcentrator comprises a silicon base 1, a silicon cover 2, two suspended membranes 3, two thin-film heaters 4, two sorptive films 5, an air inlet 6 and an air outlet 7. The preparation process of the preconcentrator is shown in FIG. 3 as follows. A silicon base 1 and a silicon cover 2 are respectively prepared on two silicon substrates 8 with thicknesses of about 500 μm. The silicon base 1 and the silicon cover 2 have the same size and micro-structure. Accordingly, the preparation process of the silicon base 1 is described as an example. Firstly, a low stress SIN film 9 (can also be silicon oxynitride film) with a thickness of about 700 nm is deposited on the front side of the silicon substrate 8 by PECVD (Plasma Enhanced Chemical Vapor Deposition). Then, a serpentine thin-film heater 4.1 with an external size of 2 mm×2 mm and a line width of about 100 μm is prepared on the SIN film by lift-off process. The sputtered thin-film heater comprises a NiCr film of about 20 nm and a Pt film of about 300 nm in sequence. Then the silicon substrate 8 under the thin-film heater 4.1 is etched away from the back side by DRIE (Deep Reactive Ion Etching) for forming a suspended membrane 3.1, an air inlet 6.1 and an air outlet 7.1. The DRIE etching comprises two steps. The air inlet 6.1 and the air outlet 7.1, with a depth of about 250 μm, a width of about 500 μm and a length of about 3 mm, are formed by the first etching step. And then the second etching step through the whole thickness of the silicon substrate 8 is carried out to form the cavity 10.1 with a size of 2.2 mm×2.2 mm, wherein the air inlet 6.1 and the air outlet 7.1 are respectively located at two sides of the cavity 10.1 and connect with each other. A sorptive film 5 is deposited on the back side of the suspended membrane 3.1 (where no thin-film heater is disposed) by mask spraying, ink-jet printing, or drop-coating method. The sorptive film can be made of various polymers. In this embodiment, the sorptive film is made of a strong hydrogen bond acidic polymer named poly methyl-{3-[2-hydroxyl-4,6-bis(trifluoromethyl)]phenyl}-propylsiloxane (abbreviated as DKAP) which can selectively adsorb the organophosphorous agents. The sorptive film can also be made of carbon black/polymer composite materials or sol-gel inorganic oxides. By the above mentioned process, the silicon base 1 is accomplished. And then the silicon cover 2 is manufactured by the same approach. Finally, the silicon cover 2 is turned upside down with respect to the silicon base 1 (back-to-back configuration), and the two parts are aligned with each other and bonded together as a whole, forming the final double-sided diaphragm micro gas-preconcentrator. In the final step, the polymer adhesive layer 11 is adapted for all kinds of the sorptive films 5, whereas the Au—Si or Al—Si bonding techniques can also be applied when the sorptive film 5 is made of high temperature materials, such as inorganic oxides. After bonding, the cavity 10.1 and 10.2 combine to the whole micro-gas chamber 12, and the sorptive film 5 is located at two inner surfaces of the micro-gas chamber, the air inlets 6.1 and 6.2 form a total air inlet 6, the air outlets 7.1 and 7.2 form a total air outlet 7. Therefore, the air inlet 6 and the air outlet 7, each having a cross section of 500 μm×500 μm, enable a large enough gas flow to pass through with an external micro air pump.

Embodiment 2

Figure 4:
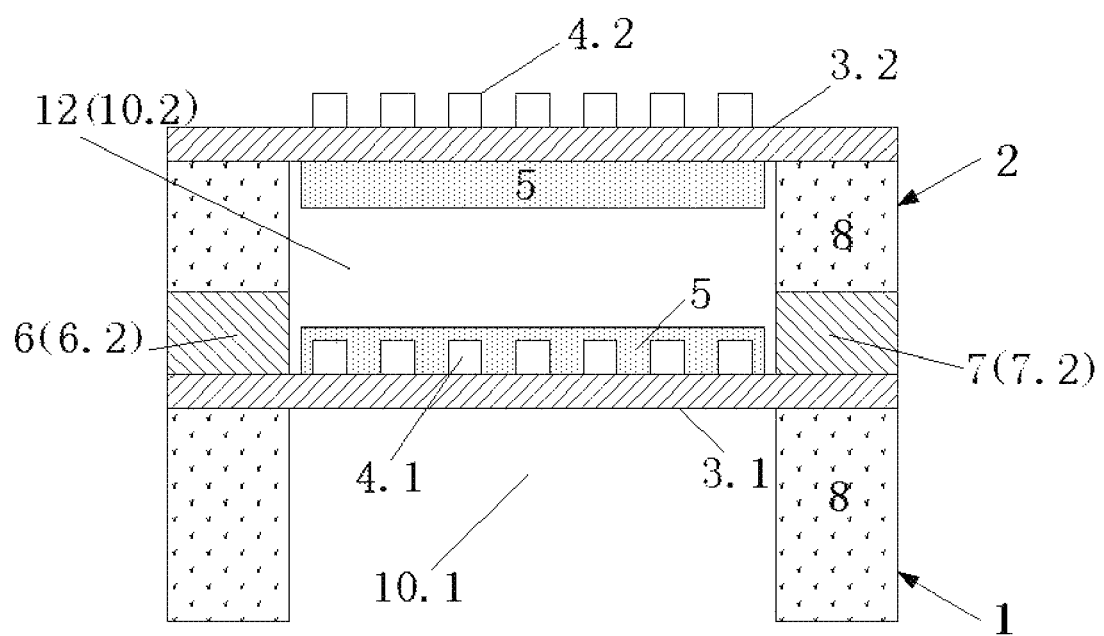
FIG. 4 is a schematic view of a double-sided diaphragm micro gas-preconcentrator according to a second preferred embodiment of the present invention.

FIG. 4 is a cross-sectional view of another double-sided diaphragm micro gas-preconcentrator according to the second preferred embodiment of the present invention. Compared with Embodiment 1, the micro-structure and micro-fabrication process of the Embodiment 2 are roughly the same, wherein the differences between them are as follows. Firstly, the silicon cover 2 is stacked on the silicon base 1 (back-on-face configuration) during bonding, so that the micro-gas chamber 12 is only made up of the cavity 10.2, and the cavity 10.1 is open. Secondly, no air inlet 6.1 and air outlet 7.1 are manufactured on the silicon base 1, and the total air inlet 6 and the total air outlet 7 are respectively made up of the air inlet 6.2 and the air outlet 7.2 on the silicon cover 2. Thirdly, the sorptive film 5 on the silicon base 1 is deposited on the thin film heater in the front side of the suspended membrane 3.1. The main advantage of Embodiment 2, with respect to Embodiment 1, is the difficulty of alignment when stacking the two silicon substrates is remarkably reduced.

Embodiment 3—Preconcentrator Array

Figure 5A:
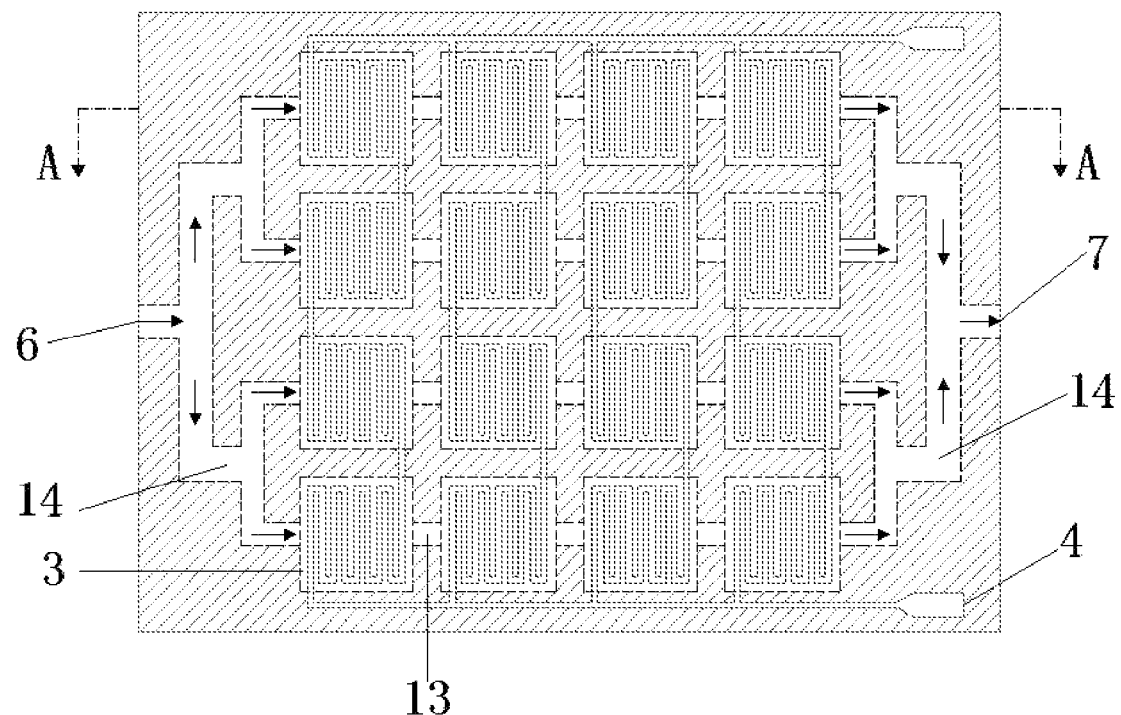
FIG. 5A is a top view of a double-sided diaphragm micro gas-preconcentrator array according to a third preferred embodiment of the present invention.
Figure 5B:
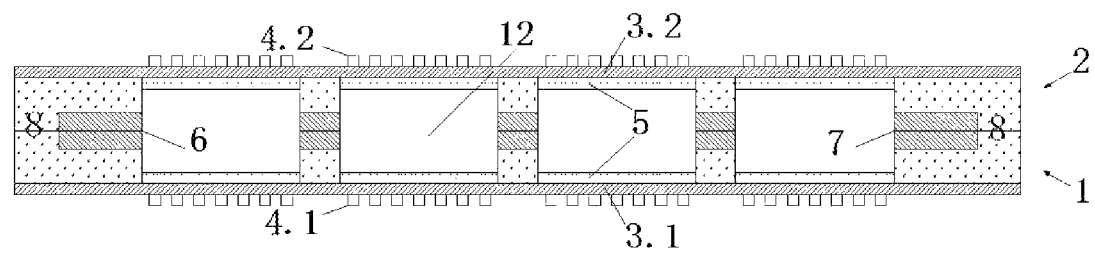
FIG. 5B is a sectional view along a direction of A-A of FIG. 5A.

FIGS. 5A and 5B are schematic diagrams of a double-sided diaphragm micro gas-preconcentrator array according to the third preferred embodiment of the present invention. Based on the first embodiment of the preconcentrator having a single micro-gas chamber shown in FIG. 2, the micro-gas chambers of the preconcentrator array in the present embodiment are expanded to sixteen. As shown in FIG. 5A, sixteen suspended membranes are provided on each of the silicon base 1 and the silicon cover 2. The thin-film heaters on the sixteen suspended membranes are connected with each other and a heater network is formed. A silicon framework with a width of about 500 μm is provided between every two suspended membranes for supporting the suspended membranes. The sixteen suspended membranes are arranged in four rows, each row comprises four suspended membranes. After bonding the silicon base 1 with silicon cover 2, sixteen micro-gas chambers are formed, the chambers of every row are connected with its adjacent partners in series by the airflow through-holes 13. Between the four row of the micro-gas chambers and the air inlet 6 or the air outlet 7, two air distribution networks 14 are disposed, so that the gas path is firstly divided into two, and then divided into four for equalizing the airflow of the four flow paths. During DRIE etching, the air distribution networks 14 and the airflow through-holes 13 are firstly etched. And then a portion of the silicon substrate 8 where the suspended membranes are located is etched away completely.

Embodiment 4—Preconcentrator Array

Figure 6A:
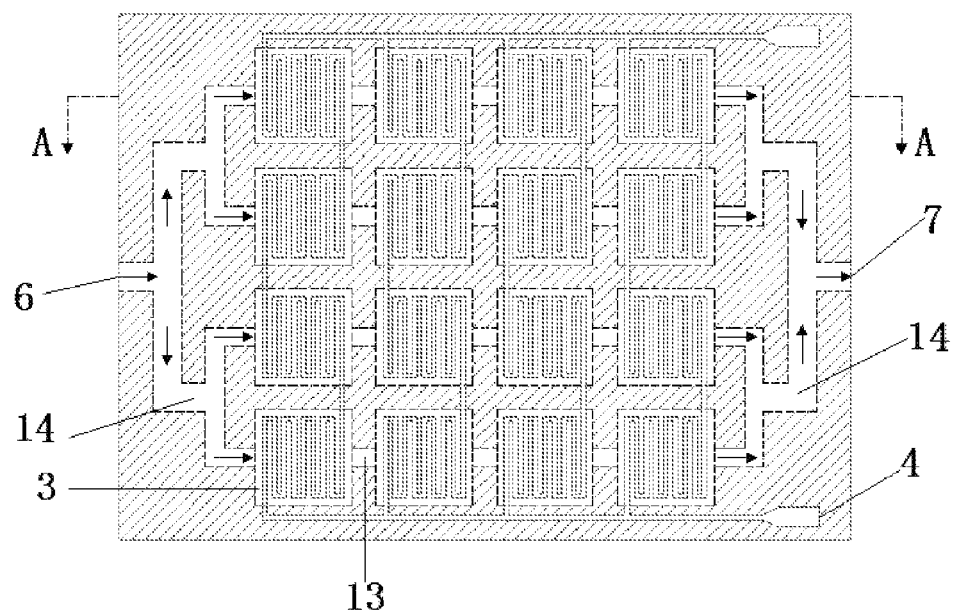
FIG. 6A is a top view of a double-sided diaphragm micro gas-preconcentrator array according to a fourth preferred embodiment of the present invention.
Figure 6B:
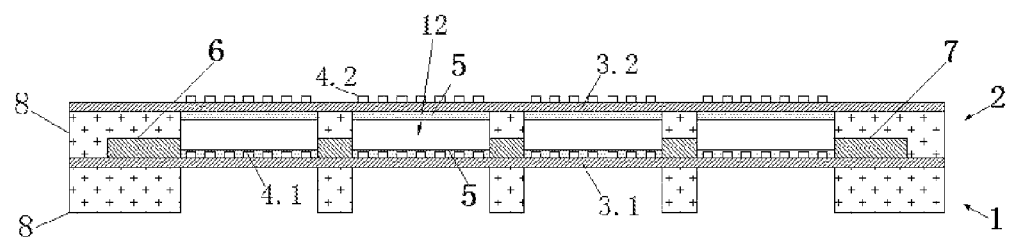
FIG. 6B is a sectional view along a direction of A-A of FIG. 6A.

FIGS. 6A and 6B are schematic diagrams of a double-sided diaphragm micro gas-preconcentrator array according to the fourth preferred embodiment of the present invention. Based on the second embodiment of the preconcentrator having a single micro-gas chamber shown in FIG. 4, the micro-gas chambers of the preconcentrator array in the present embodiment are expanded to sixteen. As shown in FIG. 6A, sixteen suspended membranes are provided on each of the silicon base 1 and the silicon cover 2. The thin-film heaters on the sixteen suspended membranes are connected with each other and a heater network is formed. A silicon framework with a width of about 500 μm is provided between every two suspended membranes for supporting the suspended membranes. The sixteen suspended membranes are arranged in four rows, each row comprises four suspended membranes. After bonding the silicon base 1 with silicon cover 2, sixteen micro-gas chambers are formed, the chambers of every row are connected with its adjacent partners in series by the airflow through-holes 13. Between the four row of the micro-gas chambers and the air inlet 6 or the air outlet 7, two air distribution networks 14 are disposed, so that the gas path is firstly divided into two, and then divided into four for equalizing the airflow of the four flow paths. During DRIE etching, a two-mask two-step process is needed for the preparation of the silicon cover 2, while a one-mask one-step process is needed for the preparation of the silicon base 1.

Figure 7:
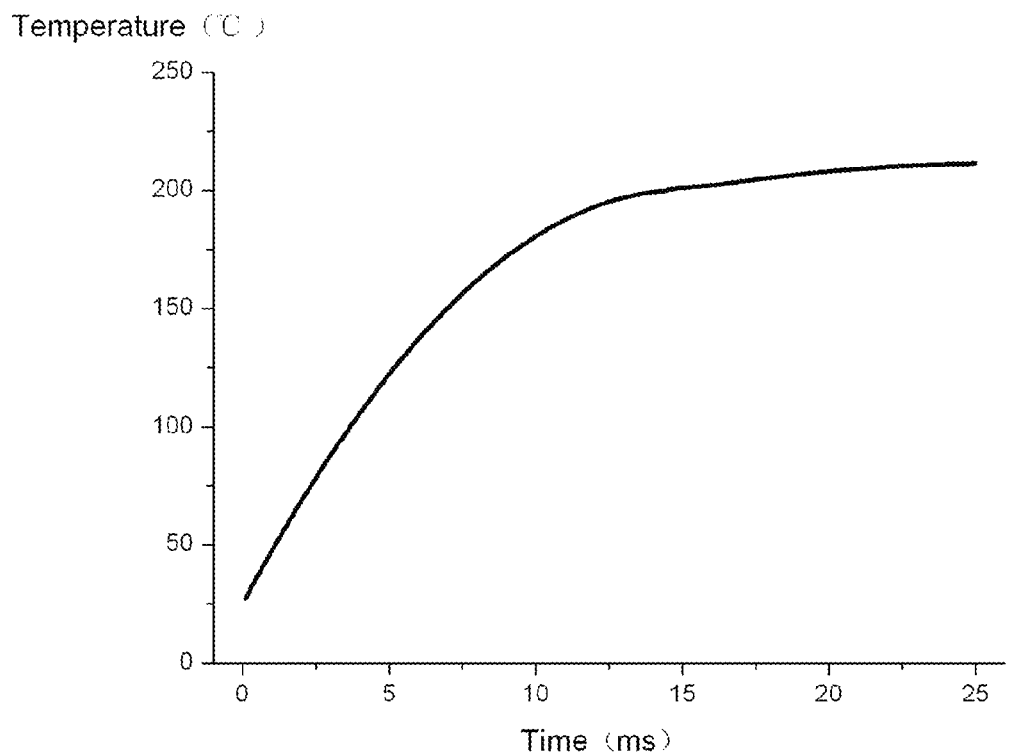
FIG. 7 shows the heating performance of a preconcentrator of the present invention.

FIG. 7 shows the heating performance of a single diaphragm, wherein the single diaphragm has a size of 2.2 mm×2.2 mm, a thickness of 1 μm, and a platinum film heater 4 and a polymer sorptive film 5 are provided on the single diaphragm. At the heating power of about 120 mW, it only needs about 15 ms for the diaphragm to increase its temperature thereof from room temperature to 200° C. Obviously, the heating performance of the preconcentrator of the present invention is similar to that of the 2D diaphragm preconcentrator disclosed by U.S. Pat. No. 6,171,378.

Figure 8:
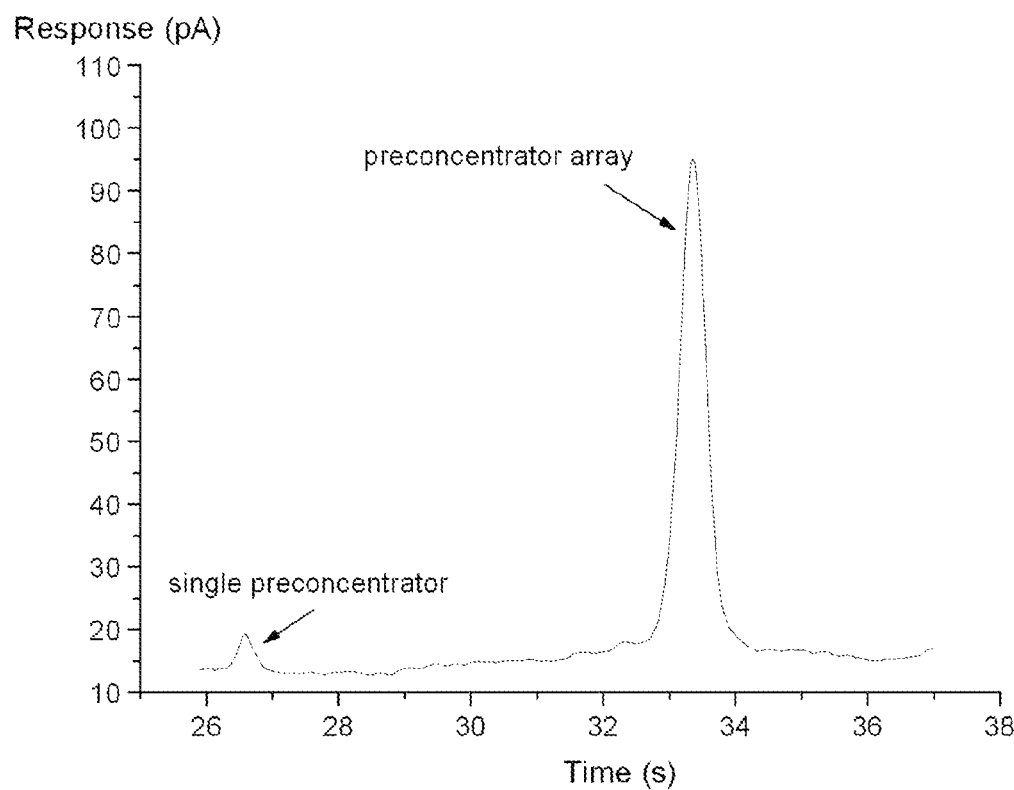
FIG. 8 shows the desorption curve of the preconcentrators of the present invention.

FIG. 8 shows the typical desorption curve of the preconcentrator of the present invention. The performance of the preconcentrator is tested by a flame ionization detector (FID) after preconcentrating 0.01 ppm DMMP for 30s and then heating for 1 s. It can be seen that the FWHM of the desorption peak of the preconcentrator (embodiment 1) is 260 ms, which is similar to that of the 2D diaphragm preconcentrator disclosed by U.S. Pat. No. 6,171,378. The FWHM of the desorption peak of the preconcentrator array (embodiment 3) is also shown in FIG. 8, although somewhat larger (405 ms), it is far superior to that of the 3D non-planar MEMS preconcentrator. The preconcentration factor of the preconcentrator array increases about 15 times with regard to the single chamber preconcentrator as shown in embodiment 1.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A double-sided diaphragm micro gas-preconcentrator with a back-on-face configuration, comprising:
   a base silicon substrate having a first suspended membrane on a front side and a first cavity on a back side of the base silicon substrate;
   a cover silicon substrate having a second suspended membrane on a front side, and a second cavity, an air inlet and an air outlet on a back side of the cover silicon substrate;

two thin-film heaters respectively disposed on a front side of the first and second suspended membranes;

a first sorptive film coated on the front side of the first suspended membrane of the base silicon substrate; and a second sorptive film coated on the back side of the second suspended membrane of the cover silicon substrate, wherein a micro-gas chamber is formed by stacking the cover silicon substrate on the base silicon substrate with a back-on-face configuration and bonding as a whole.

2. The double-sided diaphragm micro gas-preconcentrator, as recited in claim 1, wherein the suspended membrane is a film of silicon nitride or silicon oxynitride or silicon oxide or $SiN/SiO_2$ multilayer.

3. The double-sided diaphragm micro gas-preconcentrator, as recited in claim 1, wherein each of the two thin-film heaters is a serpentine metal thin film or heavily doped polysilicon thin film, and the metal thin film is made of platinum or palladium or tungsten or molybdenum or tantalum.

4. The double-sided diaphragm micro gas-preconcentrator, as recited in claim 1, wherein the sorptive film is made of polymer or a carbon black/polymer composite material or a sol-gel inorganic oxide.

5. A double-sided diaphragm micro gas-preconcentrator array, with a back-on-face configuration, comprising:

a base silicon substrate having a first multiple suspended membranes on a front side and a first multiple cavities on a back side of the base silicon substrate;

a cover silicon substrate having a second multiple suspended membranes on a front side, and a second multiple cavities, a gas distribution networks, and gas channels connecting adjacent cavities on a back side of the cover silicon substrate;

two thin-film heater networks, respectively disposed on a front side of the base and cover silicon substrate, covering all the corresponding suspended membranes, wherein each of the two thin-film heater networks comprises multiple thin-film heaters connected with each other;

a first sorptive film coated on the front side of the first multiple suspended membranes of the base silicon substrate;

a second sorptive film coated on the back side of the second multiple suspended membrane of the cover silicon substrate;

wherein multiple micro-gas chambers are formed by stacking the cover silicon substrate on the base silicon substrate with a back-on-face configuration and bonding as a whole.

6. The double-sided diaphragm micro gas-preconcentrator array, as recited in claim 5, wherein the suspended membrane is a film of silicon nitride or silicon oxynitride or silicon oxide or $SiN/SiO_2$ multilayer.

7. The double-sided diaphragm micro gas-preconcentrator array, as recited in claim 5, wherein each of the thin-film heaters is a serpentine metal thin film or heavily doped polysilicon thin film, and the metal thin film is made of platinum or palladium or tungsten or molybdenum or tantalum.

8. The double-sided diaphragm micro gas-preconcentrator array, as recited in claim 5, wherein the sorptive film is made of polymer or a carbon black/polymer composite material or a sol-gel inorganic oxide.

* * * * *